United States Patent [19]

Crisafulli, Sr., deceased

[11] Plant 4,169

[45] Dec. 27, 1977

[54] PEAR TREE

[76] Inventor: Guiseppe Crisafulli, Sr., deceased, late of Glendive, Mont., by Joseph Crisafulli, Jr., executor, P.O. Box 1051, Glendive, Mont. 59330

[21] Appl. No.: 706,742

[22] Filed: July 19, 1976

[51] Int. Cl.[2] ..... A01H 5/03

[52] U.S. Cl. ..... Plt./36

[58] Field of Search ..... Plt./36

*Primary Examiner*—Robert E. Bagwill

*Attorney, Agent, or Firm*—Merchant, Gould, Smith, Edell, Welter & Schmidt

[57] ABSTRACT

A semi-dwarf, spreading, slow to medium growing, exceptionally hardy pear tree which is resistant to fireblight and is a regular and light to moderately productive bearer of medium size, good-keeping fruit of good flavor and quality, having yellow skin with a red blush and creamy white flesh, the flesh being of smooth texture with few stone cells, juicy and subacid.

2 Drawing Figures

ORIGIN OF THE VARIETY

The present variety of pear tree was discovered in an orchard and nursery owned and operated by the discoverer near the South Side of Glendive, Mont., the origin of the variety is claimed to be a sport of the variety Bartlett in Dawson County. As the tree grew, it evidenced considerable hardiness, and as it grew to maturity and bore fruit, it further evidenced novel and distinctive characteristics. Upon recognition by the discoverer of such characteristics, the variety was asexually reproduced.

ASEXUAL REPRODUCTION OF THE VARIETY

The present variety of pear tree was asexually reproduced by the discoverer at his aforesaid orchard and nursery at Glendive, Mont. and scions of the pear tree were later delivered to the Horticultural Research Center of the University of Minnesota located in Carver County near Excelsior, Minn., which were root grafted to hardy seedling understock and grown for observation.

SUMMARY OF THE VARIETY

The present variety of pear tree is a slow to medium growing, spreading tree with relatively low stature which can be termed semi-dwarf in relation to the growth of other cultivars in the same location. In comparison, specimens of the present variety have reached 9 feet in height compared to 16 feet in height for similarly aged Patten and Golden Spice pear trees. The present variety has exhibited considerable hardiness as grown near Glendive, Mont. and Excelsior, Minn. in relation to other varieties of pear trees. The variety has not been infected with fireblight as grown in the location near Excelsior, Minn., whereas fireblight is often a problem with other varieties of pear trees grown in the general area of said location.

A red blush develops early on the green fruit of the present variety, which turns yellow with a red blush at maturity. The skin of the fruit of the present variety has a medium thickness with a smooth and glossy texture.

The flesh of the fruit of the present variety is creamy white with only a few stone cells, has a smooth and juicy texture and a good and subacid flavor. The fruit of the present variety has a good eating quality and also a good keeping quality.

BRIEF DESCRIPTION OF THE DRAWING

The drawing includes FIG. 1 which is an illustration, by photographic reproduction in color, of a branch of the present variety of pear tree, along with a fruit. FIG. 2 is a photograph of an entire tree of the variety, being approximately 15 feet in height.

DESCRIPTION OF THE VARIETY

The botanical details of this new and distinct variety of pear tree are indicated below, with color definitions (except those in common color terms) being referenced to the Horticultural Colour Chart I and II, issued by the British Colour Council in collaboration with the Royal Horticultural Society.

Tree:
- *Size.*—Small.
- *Vigor.*—Low to medium.
- *Growth.*—Spreading; medium to slow growing.
- *Form.*—Round headed.
- *Hardiness.*—Hardy; equal to Parker.
- *Production.*—Light to moderate.
- *Bearing.*—Generally regular. Ten years from planting stock on seedling rootstock.

Trunk:
- *Size.*—Medium.
- *Texture.*—Medium.

Branches:
- *Size.*—Medium.
- *Texture.*—Smooth to slightly corky.
- *Color.*—Brown-gray.
- *Lenticels.*—Number—few; Size—medium.

Leaves:
- *Size.*—Small; Length—short. 1½" to 2½" — average 2".
- *Width.*—Medium, 1½".
- *Form.*—Ovate; abruptly pointed.
- *Thickness.*—Medium.
- *Texture.*—Smooth, glabrous.
- *Margin.*—Serrated.
- *Petiole.*—Length — medium 1½" Thickness — medium; Texture — glabrous.
- *Color.*—Top side — light to medium green (Scheeles Green-860). Underside — Light to medium green (Lettuce Green-861).

Flowers:

*Blooming period.*—Approximately May 10th at Excelsior, Minn., similar to Parker.

*Size.*—Medium.

*Color.*—Pink bud, white with pink throat, margins on newly opened blossoms.

Fruit:

*Ripening period.*—September 15th to 20th at Excelsior, Minn.

*Retention.*—Hangs well.

*Size.*—Medium 3½" by 2½".

*Form.*—Turbinate to oblong — ovate pyriform.

*Stem.*—Short and thick

*Cavity.*—Narrow, smooth.

*Calyx.*—Closed, small, lobes separate at base.

*Basin.*—Small, shallow.

Skin:

*Thickness.*—Medium.

*Texture.*—Smooth, glossy.

*Color.*—Yellow (Orange Buff — 507/3); overlaid with red blush (Rose Opal — 022/1).

*Lesions.*—Pear scab lesions have been found on some fruit indicating at least partial susceptability under conditions of growth at Excelsior, Minn. The fruit shape and skin color are substantially the same as the variety Bartlett.

Flesh:

*Color.*—Creamy white, substantially the same as the variety Bartlett.

*Texture.*—Smooth; juicy with few stone cells.

*Flavor.*—Good; subacid.

*Eating quality.*—Good.

*Core.*—Medium size.

Use: Dessert; market.

Keeping quality: Good.

The Present Variety as Compared to Parker

The present variety was compared to the variety Parker at the noted location near Excelsior, Minn.

The present variety is somewhat slower growing and of less stature than the variety Parker. The round headed spreading growth habit of the present variety is similar to the variety Parker. The present variety has been winter hardy over several years at the growing locations near Glendive, Mont. and Excelsior, Minn. and has also shown no infection of fireblight during such time. The fruit of the present variety is slightly smaller than the variety Parker but the skin is smoother and the fruit is of a better flavor and eating quality.

The Present Variety as Compared to Bartlett

Other than a comparison of fruit, the present variety has not been compared to the variety Bartlett because the latter variety is not cold hardy nor generally able to survive fireblight infection at the above-mentioned location near Excelsior, Minn.

However, a fruit comparison of the present variety with the variety Bartlett indicates that the present variety is quite comparable to the variety Bartlett in its eating quality and flavor, the quality of both varieties being quite good. The fruit shape, skin color, and color of the flesh and seed cavity are substantially the same as the variety Bartlett.

Variance in Botanical Details

The pear tree and its fruit herein described may vary in slight detail due to climatic and soil conditions under which the variety may be grown; the present description being the variety as grown in Carver County near Excelsior, Minn.

I claim:

1. A new and distinct variety of pear tree, substantially as illustrated and described, which is medium to slow growing, semi-dwarf, spreading, exceptionally hardy, resistant to fireblight, and a regular and light to moderately productive bearer of medium-size good-keeping fruit, of good flavor and quality, having yellow skin with a red blush and creamy white flesh, the flesh being of smooth texture with few stone cells, juicy and subacid.

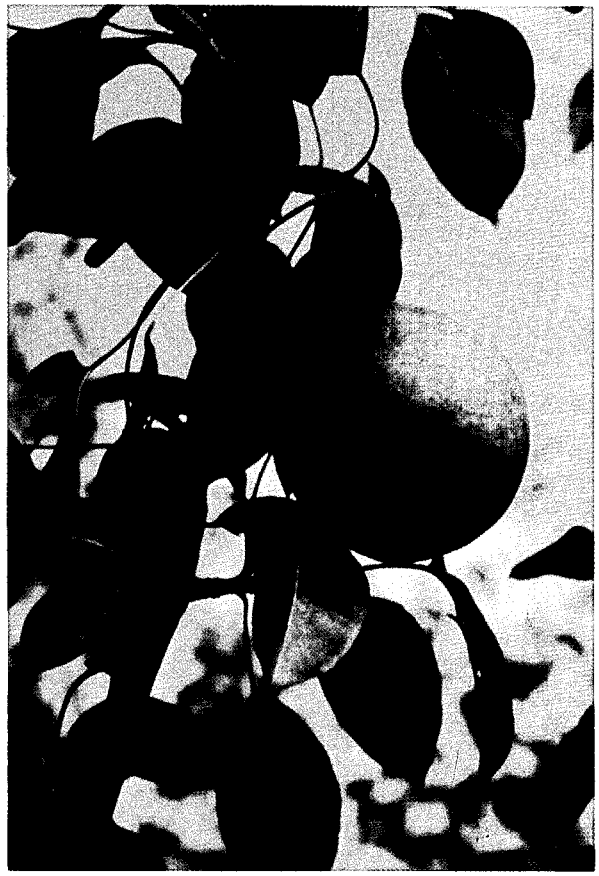

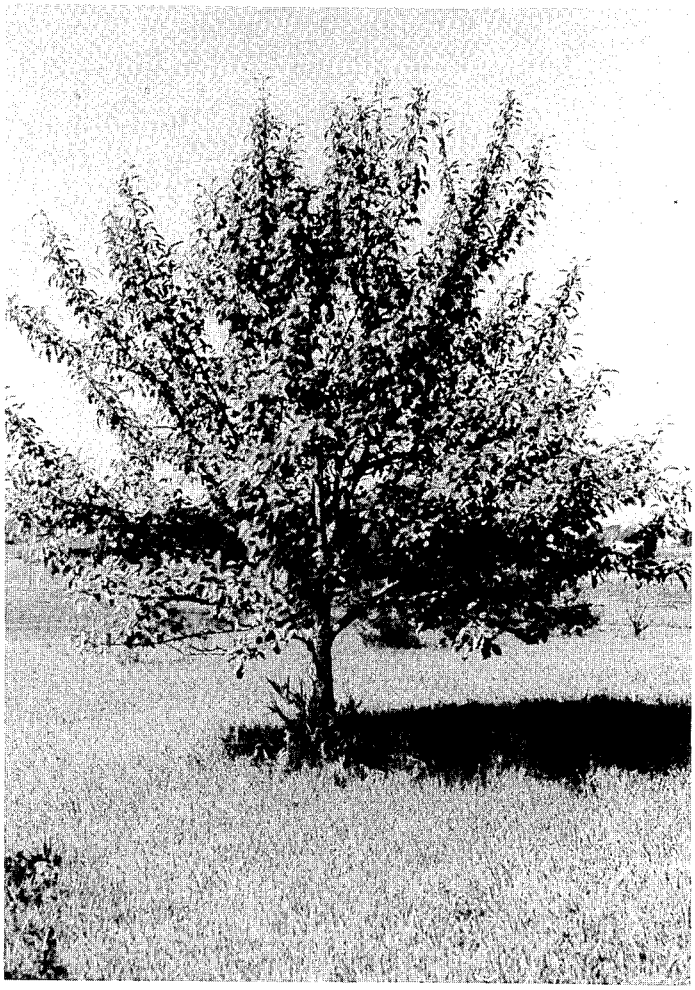

* * * * *